US00PP13792P39

(12) United States Plant Patent
Serimian et al.

(10) Patent No.: US PP13,792 P3
(45) Date of Patent: May 13, 2003

(54) NECTARINE TREE NAMED 'JUNE LION'

(76) Inventors: Donald M. Serimian, 10463 S. Del Ray Ave., Selma, CA (US) 93662; Lionel M. Serimian, 10463 S. Del Rey Ave., Selma, CA (US) 93662

( * ) Notice: Subject to any disclaimer, the term of this patent is extended or adjusted under 35 U.S.C. 154(b) by 0 days.

(21) Appl. No.: 09/770,879

(22) Filed: Jan. 25, 2001

(65) Prior Publication Data

US 2003/0014789 P1 Jan. 16, 2003

(51) Int. Cl.[7] ..... A01H 5/00

(52) U.S. Cl. ..... Plt./190
(58) Field of Search ..... Plt./190

*Primary Examiner*—Kent Bell
(74) *Attorney, Agent, or Firm*—Worrel & Worrel

(57) ABSTRACT

A new and distinct variety of nectarine tree which is somewhat remotely similar to the 'Spring Bright' nectarine tree (U.S. Plant Pat. No. 7,507), but from which it is distinguished by producing fruit which are mature for harvesting and shipment approximately five days to seven days prior to the fruit produced by the 'Spring Bright' nectarine tree in the San Joaquin Valley of central California and wherein the fruit is of high quality having a skin coloration of dark garnet red over nearly the entire surface thereof.

1 Drawing Sheet

LATIN NAME OF THE GENUS AND SPECIES OF THE PLANT CLAIMED

*Prunus persica.*

VARIETY DENOMINATION

Nectarine Tree Named 'June Lion'.

BACKGROUND OF THE NEW VARIETY

The present invention relates to a new and distinct variety of nectarine tree, *Prunus persica*, which will hereinafter be denominated varietally as the 'June Lion' nectarine tree, and, more particularly, to a nectarine tree which produces amber-yellow fleshed fruit, having a skin with a moderately uniform red blush color, which are mature for commercial harvesting and shipment approximately June 16 through July 1 in the San Joaquin Valley of central California, depending upon the particular growing year.

The discovery and development of new tree fruit varieties takes place in many areas of the world. It is a prodigious task, but one which has the potential for significant rewards. This is particularly the case in the San Joaquin Valley of central California. Much of this discovery and development has taken place in the San Joaquin Valley through more than a century of effort by a multiplicity of different individuals, business entities, research institutions, universities and the like.

Because of the efforts expended over many decades, the selection of new varieties is difficult. The new varieties must be sufficient advancements over the prior art to warrant the considerable costs required to develop such new varieties and achieve full commercialization of their product. The period of time which has transpired in such developmental efforts has resulted in the development of untold numbers of varieties of tree fruit which frequently makes selection of promising varieties difficult and distinguishing characteristics all important.

The new variety of nectarine tree of the present invention is a promising candidate for commercial development for a number of significant reasons, as will hereinafter be discussed in greater detail.

ORIGIN AND ASEXUAL REPRODUCTION OF THE NEW VARIETY

The present variety of nectarine tree hereof was discovered by the inventors in March 1993 in an experimental block located near Selma in the San Joaquin Valley of central California as a cross between the 'May Lion' (U.S. Plant Pat. No. 6,542) nectarine tree and the 'Summer Lion' (U.S. Plant Pat. No. 6,543) nectarine tree. The new variety was asexually reproduced in 1995 by the inventors by grafting bud wood of the new variety onto two scaffold limbs of 'Nemaguard' (unpatented) root stock in the experimental block. The inventors have, since that time, observed the asexually reproduced growth of the new variety and witnessed that, in all respects, the resulting progeny are identical to that of the original tree of the new variety in all respects.

SUMMARY OF THE NEW VARIETY

The nectarine tree of the new variety is characterized by producing a fruit which is ripe for commercial harvesting and shipment approximately June 16 through July 1 in the San Joaquin Valley of central California, or about five to seven days earlier than the 'Spring Bright' nectarine tree. The new variety of the present invention differs from its parents primarily in the date of fruit ripening and fruit blush color. The new variety of the present invention is perhaps most closely similar to the 'Spring Bright' nectarine tree (U.S. Plant Pat. No. 7,507), but is distinguishable therefrom by the aforementioned ripening date and in numerous other respects hereinafter to be set forth. The fruit of the new variety is more intensely colored than the fruit of the 'Spring Bright' nectarine tree being nearly completely dark garnet red while the fruit of the 'Spring Bright' nectarine tree is of a lighter orange red coloration. The fruit of the new variety is larger in size than the fruit of the 'Spring Bright' nectarine tree and is more firm in character.

BRIEF DESCRIPTION OF THE DRAWING

The drawing is a color photograph of representative portions of the new variety of nectarine tree of the present invention including fruit thereof with a first shown in bottom plan view of the apex end thereof, a second shown in side elevation displaying the suture thereof, a third shown in top plan view exposing the base thereof and a fourth sectioned and laid open to show, in one section, the pit well and flesh of the fruit and, in the other section, the stone in its natural position in the pit well and the flesh thereof; a representative stone; and representative foliage, all of the new variety of nectarine tree of the present invention.

DETAILED DESCRIPTION

Referring more specifically to the botanical details of this new variety of nectarine tree, the following has been observed under the ecological conditions prevailing at the orchard of origin which is located in an experimental block near Selma, Calif. in the United States of America. The majority of the data collected was from trees approximately four years old. All major color code designations are by reference to the *Dictionary of Color*, by Maerz and Paul, First Edition, 1930. Common color names are also occasionally employed.

TREE

Generally:

*Size.*—Approximately 14 feet in height (426.72 cm) at the end of the 1998 growing season. From 3.5 feet (106.68 cm) to 4.5 feet (137.16 cm) of the height consisted of new, current season's growth. The growth of the new variety is upright to upright-spreading in form.

*Vigor.*—Vigorous and hardy under typical climatic conditions in the San Joaquin Valley of central California.

*Figure.*—The tree was trained in a standard vase shaped configuration with a spread of 13 feet (396.24 cm) across the top of the tree.

*Productivity.*—Productive. Ranges from 1500 to 2500 fruit, depending on the season and the size of the tree.

*Regularity of bearing.*—Regular.

Trunk:

*Size.*—Thickness — Average, measuring 20.5 inches (520.7 mm) at 2.75 feet (83.82 cm) from the ground.

*Surface texture.*—Moderately coarse with a moderate amount of scarfskin present.

*Color.*—Ranges from a dark grey-brown (8-E-9 Negro Brown) to a lighter color (8-H-9 Rembrandt Brown).

*Lenticels —Numbers.*—Abundant on the surface of the trunk.

*Lenticels — Form.*—Oval and flattened horizontally.

*Lenticels — Size — Length.*—Variable.

*Lenticels — Size — Width.*—Ranges from 3 mm (0.12 inches) to 6 mm (0.24 inches).

*Lenticels — Size — Height.*—1 mm (0.04 inches) to 3 mm (0.12 inches).

*Lenticels — Surface texture.*—Often substantially callused.

Branches:

*Size —Primary Scaffold Branches.*—Range in diameter at their bases from 5.0 cm (1.95 inches) to 9.0 cm (3.51 inches) and range in height from 12 cm (4.68 inches) to 22 cm (8.58 inches) from the ground.

*Size — Upright Lateral Branches.*—Arising from scaffolds range in diameter from 4.5 cm (1.76 inches) to 7.0 cm (2.73 inches) at their bases.

*Size — Upright Spreader Branches.*—Range in diameter from 2.8 cm (1.09 inches) to 5.0 cm (1.95 inches) at their bases.

*Size — Fruiting Hanger Branches.*—Range in diameter from 0.9 cm (0.35 inches) to 1.7 cm (0.66 inches) at their bases.

*Surface texture.*—Relatively smooth on 2 year or younger wood. Current season's shoots are essentially glabrous.

*Internode — Length.*—Normal, ranging from 17 mm (0.68 inches) to 27 mm (1.08 inches) on recumbent fruiting hanger wood.

*Color — Mature branches.*—Dark brown (8-H-8 Cordovan Brown) to a lighter brown (7-E-10) Chestnut Brown).

*Color — Current season's shoots.*—Pale green (18-G-5), often with a pink-rose (5-C-8) tint on areas of the shoot directly exposed to sunlight.

*Color — ShootTips.*—New growth is a bright, glossy light green (17-L-4).

LEAVES

Size: Generally — Large. Leaf measurements have been taken from the mid-shoot area of vigorous, upright, current season's growth.

*Average length.*—Ranges from 16.7 cm (6.513 inches) to 18.3 cm (7.137 inches).

*Average width.*—Ranges from 4.4 cm (1.716 inches) to 5.3 cm (2.067 inches).

*Average thickness.*—Normal.

*Base form.*—Cuneate.

*Form.*—Lanceolate.

*Leaf tip.*—Acuminate with the apex slightly reflexed backwards and slightly twisted sideways.

*Color — Upwardly disposed surface.*—Dark green (23-J-6).

*Color —Downwardly disposed surface.*—Lighter grey-green (22-K-6 Cress Green).

*Color — Leaf Mid Vein — Downwardly disposed surface.*—Very pale green-yellow (17-I-4).

*Marginal form —Generally.*—Crenate, with large, relatively uniform crenations.

*Leaf margin.*—Slightly undulate.

*Glandular characteristics.*—From 1 to 3 glands are present on the very base of the leaf margin (most frequently 2). No additional glands are usually present on the surface of the petiole itself.

*Glands —Size.*—Gland size ranges from 1.0 mm (0.04 inches) to 1.5 mm (0.06 inches) in length and from 0.5 mm (0.02 inches) to 1.0 mm (0.04 inches) in diameter.

*Glands — Form.*—Distinctly reniform.

*Glands — Position.*—Alternate.

*Glands — Color.*—Yellow-green (17-K-2) with a darker more brownish center.

*Petiole — Size.*—Normal.

*Petiole — Length.*—Ranging from 7 mm (0.28 inches) 11 mm (0.44 inches).

*Petiole — Thickness.*—Varies from 1.5 mm (0.6 inches) to 2.0 mm (0.08 inches).

*Petiole — Color.*—Pale green (17-J-5), slightly darker green (17-K-6) on the surface of the ridges above the petiole groove.

*Stipules.*—Early deciduous.
*Stipules — Size.*—Relatively large.
*Stipules — Size — Length.*—9 mm (0.36 inches) to 11 mm (0.44 inches).
*Stipules — Form.*—Linear Lanceolate.
*Stipules — Margins.*—Very serrate with dark brown trichomes along the margins.
*Stipules — Color.*—Pale yellow-green (17-J-4), becoming darker with age.

Flower:

*Generally.*—The following description was developed on Mar. 8, 1999. The chilling hours for the 1998/1999 winter season were comparatively high for the growing area at 1331 hours.
*Date of bloom.*—Average in relation to other nectarine cultivars in the same fruit growing area. The date of full bloom was Mar. 10, 1999.
*Flow buds.*—Hardy under typical growing conditions in the San Joaquin Valley of central California.
*Flower buds — Size.*—Bud ranges from 4.0 mm (0.16 inches) to 5.5 mm (0.22 inches) in length and from 3.0 mm (0.12 inches) to 4.0 mm (0.16 inches) in diameter.
*Flower buds — Form.*—Conic.
*Flower buds — Scales — Color.*—Dark brown (8-H-4).
*Flower buds.*—Slightly appressed to the bearing stem.
*Flower buds — Surface texture.*—Highly pubescent.
*Flowers — Generally.*—Large in size and of the "showy" type.
*Flowers — Diameter.*—When fully expanded, ranges from 32 mm (1.28 inches) to 46 mm (1.84 inches).
*Bloom quantity.*—Moderately dense on one year old wood. Flower bud frequency per node varies from one to two buds, most frequently two.
*Petals — Size — Generally.*—Large.
*Petals — Size — Length.*—16 mm (0.64 inches) to 20 mm (0.8 inches).
*Petals — Size — Width.*—14 mm (0.56 inches) to 18 mm (0.72 inches).
*Petals — Form.*—Broadly ovate.
*Petals — Number.*—Petal count is five.
*Petals — Color — Immature.*—Light pink (1-C-1), darker basally (1-I-1) on both upper and lower surfaces with the upper surface being more glossy and the lower surface being more dull.
*Petals — Color — Mature.*—Darken with age to a more intense pink (1-D-1), darker basally (1-I-3) on both upper and lower surfaces with the upper surface being more glossy and the lower surface being more dull.
*Petal claw — Form.*—Truncate.
*Petal claw.*—Short.
*Petal claw — Size — Length.*—Averaging 1.0 mm (0.04 inches).
*Petal claw — Size — Width.*—1.5 mm (0.06 inches).
*Petal margins.*—Slightly cupped and moderately undulate, especially laterally.
*Petal apex.*—Domed and vary from smooth to undulate along the margin.
*Pedicel.*—Short.
*Pedicel — Size — Length.*—Averaging 1.0 mm (0.04 inches).
*Pedicel — Size — Thickness.*—Ranging from 1.5 mm (0.06 inches) to 2.0 mm (0.08 inches).
*Pedicel — Color.*—Bright green (19-L-7).
*Pedicel — Surface.*—Shiny and glabrous.
*Floral nectaries — Color.*—Orange (11-L-8 Nugget Bronze), becoming slightly more dark and dull with age.
*Calyx — External surface.*—Glabrous, rugose and veined.
*Calyx — External color.*—Green (19-L-7) basally, becoming a mottled maroon to solid maroon (7-E-5 Mauve Rose) next to the sepal attachment.
*Sepal — Surface.*—Pubescent.
*Sepal — Size.*—Ranges from 4.5 mm (0.18 inches) to 6.0 mm (0.24 inches) in length and from 4.5 mm (0.18 inches ) to 5.0 (0.2 inches) in width.
*Sepal — Form.*—Conic.
*Sepal — External color.*—Generally light maroon (7-E-3) with green striping (20-K-6 Piquant Green).
*Anthers.*—Plump.
*Anthers — Size.*—Average.
*Anthers — Color — Ventrally.*—Red-orange (5-J-11 Korea Red).
*Anthers — Color — Dorsally.*—Buff (11-J-3).
*Pollen.*—Abundant.
*Pollen — Color.*—Yellow-gold (9-L-3).
*Stamen.*—Usually slightly shorter than the pistil.
*Stamen — Length.*—Variable. Ranges from 9 mm (0.36 inches) to 15 mm (0.6 inches).
*Filament — Color.*—Very pale pink (1-C-1), darkening with age to a deep rose (1-J-5).
*Pistil — Size.*—Average.
*Pistil — Number.*—Most frequently one pistil per flower, infrequently, less than 5 percent of the time, two pistils per flower.
*Pistil — Size — Length.*—Including the ovary ranges from 17 mm (0.68 inches) to 21 mm (0.84 inches).
*Style — Color.*—Pale yellow-green (17-H-2).
*Style — Surface.*—Glabrous.
*Ovary — Color.*—Darker bright green (17-L-7 Viridine Yellow).

FRUIT

Maturity when described: Ripe for commercial harvesting and shipment approximately June 16 to July 1 near Selma in the San Joaquin Valley of central California. In 1998, the instant variety was ripe for commercial harvesting and shipment approximately June 25 to July 1 which is consistent with the fact that in 1998, the maturity dates for tree fruit were, over all, about ten to twelve days later than the average maturity dates for a given year.

Size:

*Generally.*—Large.
*Average diameter in the axial plane.*—Ranges from 62 mm (2.48 inches) to 65 mm (2.6 inches).
*Average diameter in the suture plane.*—Ranges from 67 mm (2.68 inches) to 75 mm (3 inches).
*Average diameter to the cheek plane.*—Ranges from 66 mm (2.64 inches) to 71 mm (2.84 inches).
*Brix level.*—Ranges from 13 to 18 degrees at normal commercial maturity.
*Form — uniformity.*—Good.
*Form — lateral aspect.*—Generally ovate in lateral aspect.
*Form — apical aspect.*—Variable from globose to oval.
*Form — symmetry.*—Most frequently asymmetrical with one fruit half slightly larger than the other.
*Suture — generally.*—Visible from base to apex. Deeper over the basal shoulder and within the stem cavity. The suture deepens over the apical shoulder and is substantially depressed on the ventral side of the apex. No callusing or stitching is present on the suture line.

*Suture line — Color.*—Streaked and slightly lighter than the darkest blush coloration surrounding the suture. Ranges from (5-L-10 Chimney Red) to a darker red (6-L-11 Egyptian Red).

*Ventral surface — Generally.*—Relatively smooth and slightly lipped on one side.

*Stem cavity — Generally.*—Average in size. Often a line of ground color yellow (10-L-2 Aureolin Yellow) is present in or around the base of the fruit where the bearing stem was pressed against the fruit surface.

*Stem cavity — Width.*—Ranges from 20 mm (0.8 inches) to 28 mm (1.12 inches).

*Stem cavity — Depth.*—Ranges from 12 mm (0.48 inches) to 14 mm (0.56 inches).

*Stem cavity — Length.*—Ranges from 28 mm (1.12 inches) to 32 mm (1.28 inches).

*Stem cavity — Shape.*—Oval.

*Stem — Length.*—Varies from 7 mm (0.28 inches) to 9 mm (0.36 inches).

*Stem — Thickness.*—Ranges from 5 mm (0.2 inches) to 6 mm (0.24 inches).

*Stem — Color.*—Pale green-yellow (18-J-3).

*Base — Form.*—Varies from rounded to slightly truncate.

*Base angle.*—Variable, from slightly oblique to at right angle to the fruit axis.

*Apex — Shape.*—Slightly raised and domed.

*Pistil point — Position.*—Oblique.

*Weight.*—Ranges from 195 grams (6.83 ounces) to 285 grams (9.98 ounces).

Skin:

*Thickness.*—Average.

*Texture.*—Fully glabrous. The skin is tightly attached to the fruit flesh at commercial maturity.

*Acidity.*—Relatively neutral.

*Tendency to crack.*—No tendency for the skin to crack or split has been observed.

*Blush color.*—Underlying blush color ranges from a bright red (5-L-11 Brickdust Red) to a slightly darker (6-L-8 Dark Cardinal Red).

*Blush — Form.*—Combination of an underlying washed blush overlain with darker striping and dappling.

*Underlying washed blue color.*—Ranges from a bright red (5-L-11 Brickdust Red) to a slightly darker (6-L-8 Dark Cardinal Red).

*Overlying blush color.*—Striping and dappling is a darker, deeper red (6-L-9 Garnet Red). Numerous light colored (10-L-2 Aureolin Yellow) dots can be present, most frequently at the apex and over the apical shoulders.

*Ground color — Generally.*—Present over 2 percent to 10 percent of the fruit surface. Most often, the ground color is found in the stem cavity or where the cavity shoulder has been pressed by the bearing branch.

*Ground color.*—Bright yellow-amber (10-L-2 Aureolin Yellow).

Flesh:

*Flesh color.*—Uniform amber-yellow (10-K-3 Lemon Yellow) from the skin inwards to the stone cavity. At advanced maturity, a light amount of red (5-K-11 Moroccan Red) flecking can be present in the flesh in the proximity of the skin.

*Surface of pit cavity.*—A moderate number of yellow (10-K-3 Lemon yellow) fibers are present in the flesh and on the surface of the stone cavity. No red coloration is present in the flesh or within the stone cavity at commercial maturity.

*Flavor.*—Mild and well balanced.

*Aroma.*—Has only a slight, pleasant aroma.

*Texture.*—Firm and fine.

*Fibers — numbers.*—Moderate.

*Ripening.*—Evenly.

*Eating quality.*—Good.

Stone:

*Attachment.*—Semi-clingstone, held tightly to the flesh at commercial maturity, but breaking free of the stone at advanced maturity.

*Fibers — Numbers.*—A few fine, yellow (10-K-3 Lemon yellow) fibers are present.

*Size — Generally.*—Medium.

*Size — Length.*—Ranges from 36 mm (1.44 inches) to 44 mm (1.76 inches).

*Size — Width.*—Ranges from 28 mm (1.12 inches) to 34 mm (1.36 inches).

*Size — Thickness.*—Ranges from 22 mm (0.88 inches) to 26 mm (1.04 inches).

*Form — Generally.*—Variable from oval to slightly obovate.

*Apex — Shape.*—Acute with a sharp tip. The apical shoulder is heavily eroded on the dorsal side.

*Color — Dry.*—Buff brown (11-H-5). Areas of the stone near the apex are slightly darker.

*Base — Shape.*—Variable from at right angle to slightly oblique to the stone axis.

*Sides — Generally.*—Most frequently uneven but at times are only slightly so.

*Hilum.*—Heavily eroded and with a moderately thick collar.

*Hilum — Size.*—Ranges from 3.0 mm (0.12 inches) to 4.5 mm (0.18 inches) in width and from 5.5 mm (0.22 inches) to 7.0 mm (0.28 inches) in length.

*Hilum — Form.*—Oval.

*Surface.*—Generally deeply pitted and grooved.

*Ridges and grooves.*—Most apparent over the apical shoulders laterally.

*Pits.*—Most apparent over the stone sides laterally.

*Ventral edge.*—Relatively wide.

*Ventral edge — Size — Width.*—Ranges from 6 mm (0.24 inches) to 8 mm (0.32 inches) at mid suture.

*Ventral edge — Wings.*—Most apparent near mid suture, converging apically.

*Dorsal edge.*—Relatively tight groove is present along the dorsal edge, most apparent from the base to slightly above mid stone.

*Dorsal ridges.*—Strong dorsal ridges are most apparent from the base to slightly above mid stone.

*Upper dorsal shoulder.*—Heavily eroded, at times concave in form near the apex.

*Tendency to split.*—No tendency to split has been observed.

Keeping and shipping quality: Outstanding.

Resistance to disease: No unusual susceptibility or resistance to diseases common to nectarine trees.

Resistance to pests: No unusual susceptibility or resistance to pests.

Winter hardiness: Hardy under typical San Joaquin Valley climatic conditions with temperatures that seldom drop below 20 degrees F.

Although the new variety of nectarine tree possesses the described characteristics noted above as a result of the growing conditions prevailing near Selma in the San Joaquin Valley of central California in the United States of America, it is to be understood that variations of the usual magnitude and characteristics incident to changes in growing conditions, irrigation, fertilization, pruning, pest control, climatic variation and the like are to be expected.

Having thus described and illustrated our new variety of nectarine tree, what we claim as new and desire to be secured by Plant Letters Patent is:

1. A new and distinct variety of nectarine tree substantially as illustrated and described which is somewhat remotely similar to the 'Spring Bright' nectarine tree (U.S. Plant Pat. No. 7,507), but from which it is distinguished by producing fruit which are mature for commercial harvesting and shipment approximately five days to seven days prior to the 'Spring Bright' nectarine tree, in the San Joaquin Valley of central California and which have a distinctive dark garnet red coloration over virtually its complete skin surface.

* * * * *

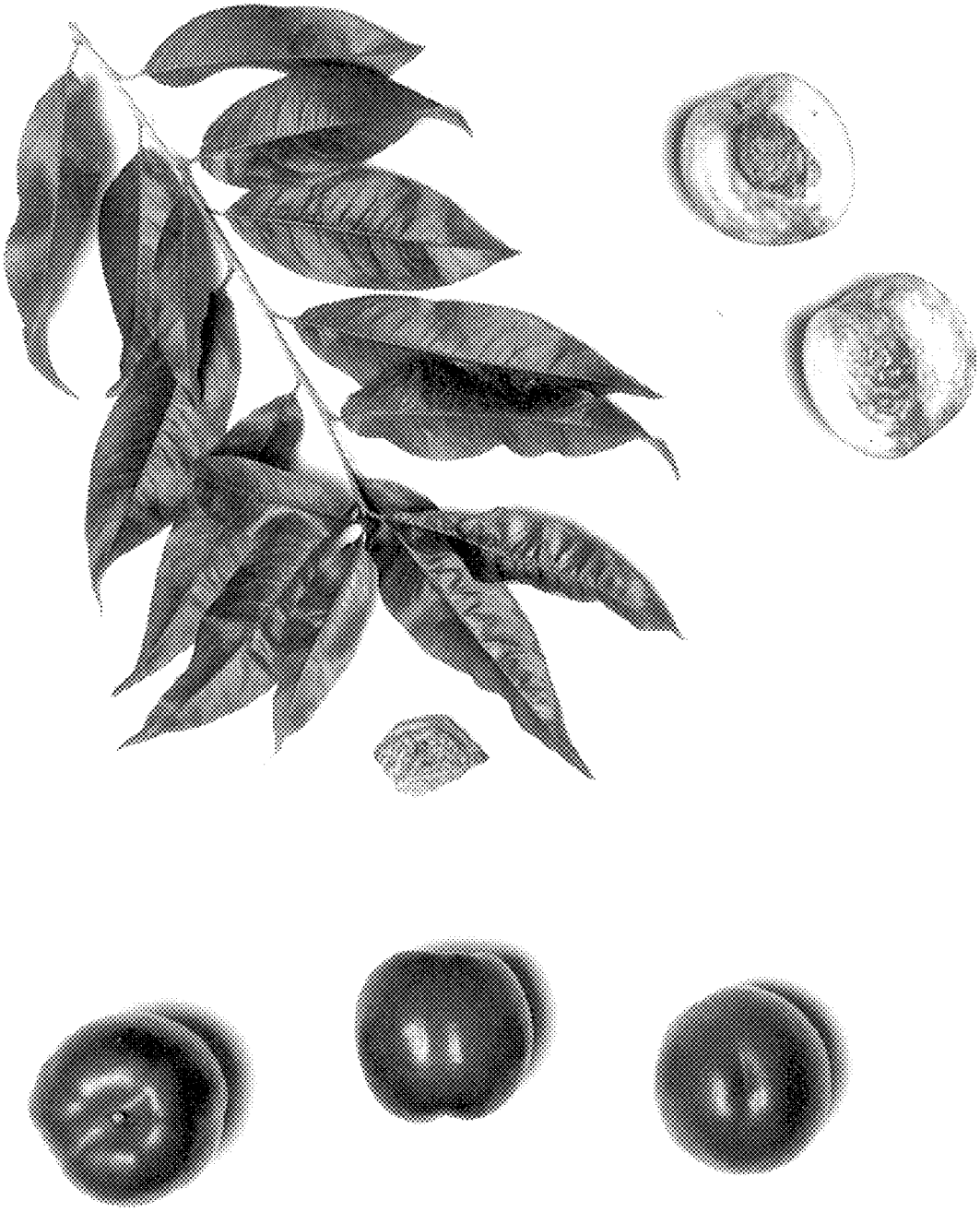

UNITED STATES PATENT AND TRADEMARK OFFICE

CERTIFICATE OF CORRECTION

PATENT NO. : PP 13,792 P3
DATED : May 13, 2003
INVENTOR(S) : Serimian et al.

It is certified that error appears in the above-identified patent and that said Letters Patent is hereby corrected as shown below:

Title page,
Item [76], 2nd Inventors address, delete “Ray” substitute -- Rey --.

Column 5,
Line 18, delete “Flow” and substitute -- Flower --.

Column 7,
Line 48, delete “blue” and substitute -- blush --.

Signed and Sealed this

Ninth Day of September, 2003

JAMES E. ROGAN
*Director of the United States Patent and Trademark Office*